United States Patent [19]

Hori et al.

[11] Patent Number: 5,800,689

[45] Date of Patent: Sep. 1, 1998

[54] OXYGEN CONCENTRATION DETECTOR

[75] Inventors: Makoto Hori, Ogaki; Toshimi Miyamoto, Okazaki; Kenji Fukaya, Chiryu; Masahiro Hamaya, Anjo; Minoru Ohta, Okazaki; Naoto Miwa, Tsushima, all of Japan

[73] Assignee: Nippondenso Co., Ltd., Japan

[21] Appl. No.: 609,634

[22] Filed: Mar. 1, 1996

[30] Foreign Application Priority Data

Mar. 2, 1995  [JP]  Japan .................. 7-070963

[51] Int. Cl.⁶ .......................... G01N 27/407
[52] U.S. Cl. .................. 204/428; 204/421; 204/424; 204/426; 204/427
[58] Field of Search ................. 204/421–429

[56] References Cited

U.S. PATENT DOCUMENTS

| | | | |
|---|---|---|---|
| 3,847,777 | 11/1974 | Haddad et al. | 204/415 |
| 3,935,089 | 1/1976 | Togawa et al. | 204/429 |
| 4,021,326 | 5/1977 | Pollner et al. | 204/429 |
| 4,107,019 | 8/1978 | Takao et al. | 204/426 |
| 4,383,906 | 5/1983 | Sano et al. | 204/428 |
| 4,402,820 | 9/1983 | Sano et al. | 204/429 |
| 4,559,126 | 12/1985 | Mase et al. | 204/426 |
| 5,089,133 | 2/1992 | Kato et al. | 204/427 |

FOREIGN PATENT DOCUMENTS

| | | |
|---|---|---|
| A-59-221971 | 12/1984 | Japan . |
| A-H5/26842 | 2/1993 | Japan . |
| A-H5/149914 | 6/1993 | Japan . |
| A-H5/312707 | 11/1993 | Japan . |

*Primary Examiner*—T. Tung
*Attorney, Agent, or Firm*—Cushman Darby & Cushman Intellectual Property Group of Pillsbury Madison & Sutro, LLP

[57] ABSTRACT

An oxygen concentration detector has a detecting element comprising a solid electrolyte inserted into a housing and heating means for heating the detecting element, and the outer surface of the detecting element is provided with a surface layer, the contact angle of the surface layer being larger than the contact angle of the outer surface of the detecting element with which the surface layer directly contacts.

16 Claims, 11 Drawing Sheets

OXYGEN CONCENTRATION DETECTOR

BACKGROUND OF THE INVENTION

1. Field of the Invention

The present invention relates to an oxygen concentration detector to be used for automobile engine air-fuel ratio control, etc.

2. Description of the Related Art

Most conventional oxygen concentration detectors used to detect the oxygen concentration of exhaust gas emitted from automobile engines have been oxygen concentration-based electromotive systems comprising a detecting element with a $ZrO_2$ solid electrolyte and a heater situated inside the detecting element.

Figure 1:
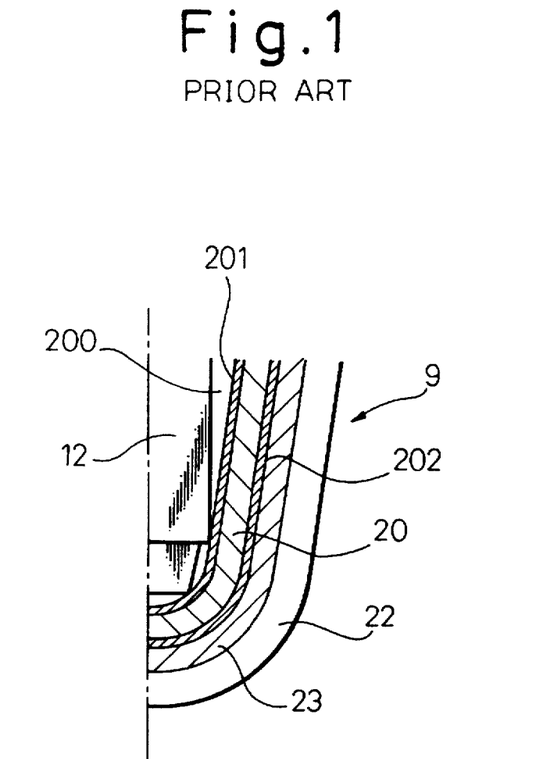
FIG. 1 is a schematical cross-sectional view of a detecting element according to the prior art.

As shown in FIG. 1, the detecting element 9 consists of a basically test tube-shaped solid electrolyte 20 provided with an inner electrode 201 made of a platinum film on the inside and an outer electrode 202 made of a platinum film on the outside. On the surface of the outer electrode 202 there are provided a coating layer 23 made of spinel and a trap layer 22 made of alumina, for protection of the outer electrode 202.

This oxygen concentration detector is usually placed in an exhaust pipe between the engine and the catalytic converter which serves to purify the exhaust gas.

In recent years there has been a trend toward constructing oxygen concentration detectors further downstream than in the past, due to the rise of 2-bank vehicles which have come with higher performance engines. Also, for detection of degradation by catalytic converters in accordance with OBDII regulations, etc., or for A/F control compensation, it is becoming increasingly opportune to install oxygen concentration detectors downstream of the catalytic converters.

As a result, when the engine is started, the oxygen concentration detector comes into contact with water due to condensation and residue of water in the exhaust pipe, which increases the water-induced cracking of the detecting element upon thermal shock.

With the stricter exhaust gas regulations, it has also become necessary to reduce cold emissions. Consequently, it has become opportune to use low-heat-capacity layered detecting elements or high-output heaters. This has resulted in even greater proneness to water-induced cracking because of the improved heating-up efficiency of the detecting elements.

As a way of overcoming these problems, a structure with a protective cover covering the side of the detecting element has been constructed in the following manner.

That is, the protective cover has a double-layered structure. A drainage hole is provided at the bottom of the protective cover. The area of the exhaust gas inlet holes in the protective cover and the number of holes are optimized to control the penetration of water droplets. The locations of the exhaust gas inlet openings in this double-layered protective cover are modified to give the inside of the cover a labyrinth structure.

However, since this construction results in a complex internal structure of the protective cover, it is difficult for the exhaust gas to reach the detecting element. This results in problems of engine control, owing to impaired response of the oxygen concentration detector and poorer stability during emission and idling.

In light of these problems, it is an object of the present invention to provide an oxygen concentration detector wherein water-induced cracking does not occur in the detecting element.

SUMMARY OF THE INVENTION

The present inventors have elucidated the mechanism of element cracking.

Figure 2:
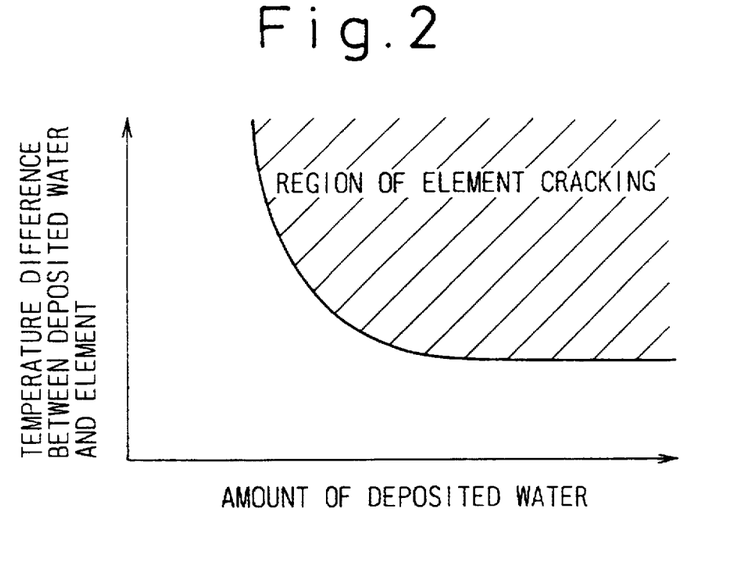
FIG. 2 is a graph showing the region of element cracking based on the relationship between the amount of contacting water and the temperature difference between the deposited water and the element.

The results are shown in FIG. 2.

FIG. 2 shows the zone of element cracking based on the relationship between the amount of water deposited onto the element surface and the temperature difference between the adhered water and the element.

The present inventors have found, as clearly shown in FIG. 2, that when the initial amount of water on the element surface is exceedingly small, cracking does not occur in the element even with a somewhat large temperature difference between the element and the water. In other words, it was found that since element cracking does not occur when the amount of water deposited onto the element surface is small, the element cracking may be prevented by employing means to reduce the amount of water contacting the element surface.

Thus, the present invention employs a construction which provides on the element surface a novel layer with a water-repellent surface layer having a large contact angle, which has not been used in conventional detecting elements.

The present invention is an oxygen concentration detector which has a detecting element comprising a solid electrolyte inserted into a housing and heating means for heating the detecting element, wherein the outer surface of the detecting element is provided with a surface layer, and the contact angle of the surface layer is larger than the contact angle of the outer surface of the detecting element with which the surface layer directly contacts.

Between the detecting element and the surface layer there is provided a protective layer which protects the electrode provided on the surface of the detecting element and has a contact angle which is smaller than the contact angle of the surface layer, while a trap layer may also be placed between the protective layer and the surface layer, having a larger porosity than that the porosity of the protective layer and a smaller contact angle than the contact angle of the surface layer.

The above-mentioned surface layer preferably has a thickness of 20 to 500 µm. If the thickness is less than 20 µm it may become impossible to prevent water-induced cracking. Conversely, if the thickness is greater than 500 µm, the adhesive strength of the surface layer to the detecting element may become weaker, tending to result in peeling of the surface layer.

The porosity of the surface layer is preferably 20 to 90%. A void content of less than 20% may result in loading of the surface layer by contamination in the gas being measured. Conversely, a porosity of greater than 90% may result in lower strength of the surface-layer.

The surface layer comprises particles of one of more types selected from the group consisting of BN, $CaF_2$, NbC, $ZrB_2$, $TiB_2$ and talc.

The surface layer also preferably contains alumina. As described below, the alumina is used as a binder during formation of the surface layer. The content of alumina with respect to the total surface layer is preferably within 20 wt %. If the content exceeds 20 wt % it may become impossible to prevent water-induced cracking.

The oxygen concentration detector may be constructed so that heating means is situated outside the detecting element, in which case the outermost surface of the heating means and the detecting element may be given a surface layer with a contact angle larger than the solid electrolyte.

The oxygen concentration detector may also have a detecting element made of a solid electrolyte in the form of a cylinder which is open at one end and closed at the other, a measuring electrode provided on the surface of the detecting element, and a protective layer provided on the measuring electrode, in which case there may be provided a surface layer which covers the protective layer and has a contact angle larger than the contact angle of the protective layer. In this oxygen concentration detector as well, a trap layer may be placed between the protective layer and the surface layer, having a larger porosity than the porosity of the protective layer and a smaller contact angle than the contact angle of the surface layer.

The oxygen concentration detector may also have a detecting element made of a solid electrolyte in the form of a sheet, an electrode formed on the surface of the detecting element, and a protective layer formed on the surface of the electrode, in which case it may also comprise a first surface layer provided so as to cover the protective layer, having a larger contact angle than the contact angle of the protective layer, a heating element layered on the detecting element to heat the detecting element, and a second surface layer provided on the outer surface of the heating element, having a larger contact angle than the contact angle of the heating element surface. In this oxygen concentration detector as well, a trap layer may be placed between the protective layer and the first surface layer, having a larger porosity than the porosity of the protective layer and a smaller contact angle than the contact angle of the first surface layer.

Figure 3:
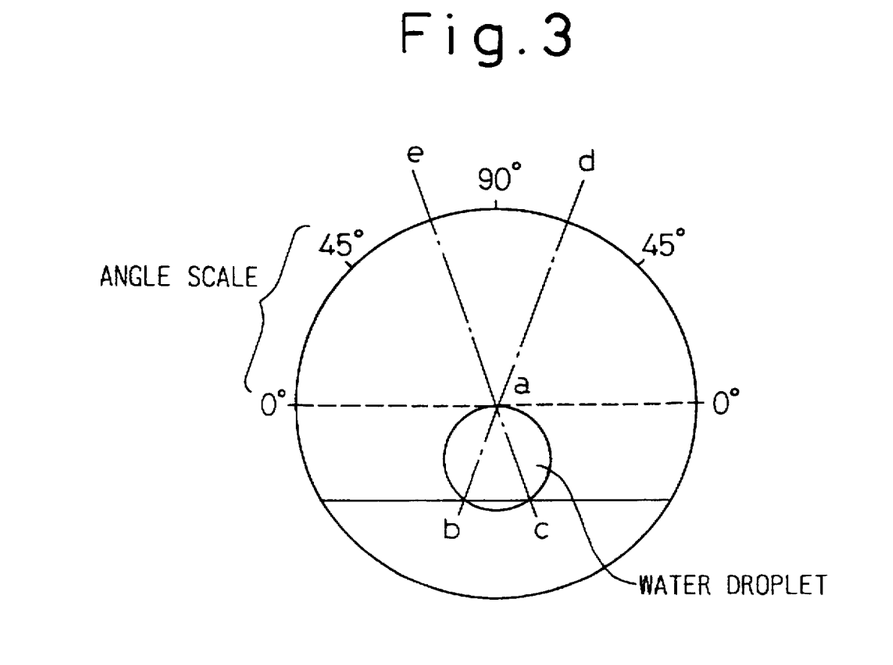
FIG. 3 is an illustration of the method of measuring the contact angle.

The method of measuring the contact angle according to the present invention will now be explained with reference to FIG. 3.

According to the invention, a 5 µl water droplet is first dropped onto the surface of a test piece using a syringe. The water droplet is then examined under a contact angle-measuring microscope. The center line of the microscope lens is aligned with the top of the water droplet indicated as "a" in the drawing. The angles are then read at points "d" and "e" at the periphery-crossing ends of the radii passing through the center (top) "a" from the contact points "b" and "c" of the water droplet with the measuring surface. Finally, the sum of the two angles which were read is taken as the "contact angle" according to the invention. In cases where the test piece is in powder form, it is evenly applied onto double-sided tape for the measurement.

The oxygen concentration detector according to the present invention is provided with a surface layer with a large contact angle on the outside of the detecting element.

Consequently, even when the oxygen concentration detector contacts water in the form of water droplets from the outside, the water droplets are repelled by the surface layer to alleviate the heat shock on the solid electrolyte due to the water droplets, and thus no water-induced cracking occurs in the detecting element.

Thus, according to the invention there is provided an oxygen concentration detector wherein water-induced cracking does not occur in the detecting element.

EXAMPLE 1

An oxygen concentration detector 1 according to an embodiment of the present invention will now be explained with reference to FIGS. 4 and 5.

Figure 4:
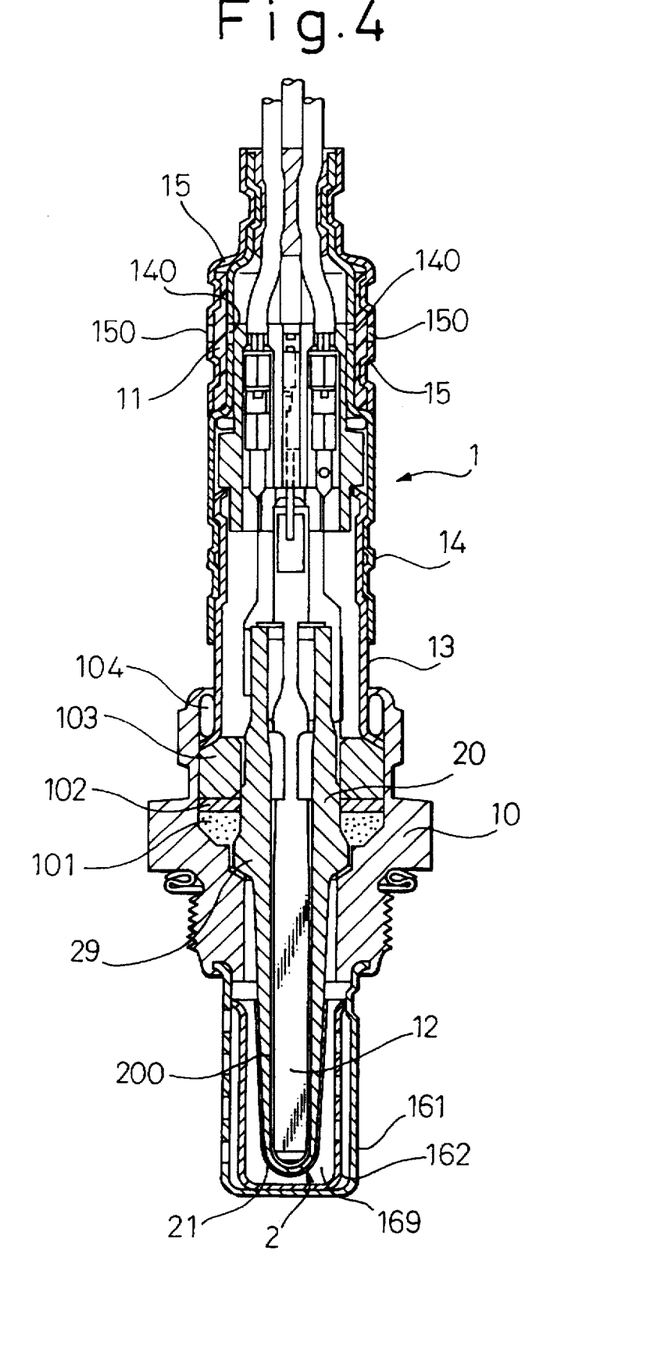
FIG. 4 is a cross-sectional illustration of the oxygen concentration detector of Example 1.

As shown in FIG. 4, this embodiment of the oxygen concentration detector 1 includes a detecting element 2 comprising a solid electrolyte 20 inserted in a housing 10, and a heater 12 as the above-mentioned heating means situated inside the detecting element 2.

Figure 5:
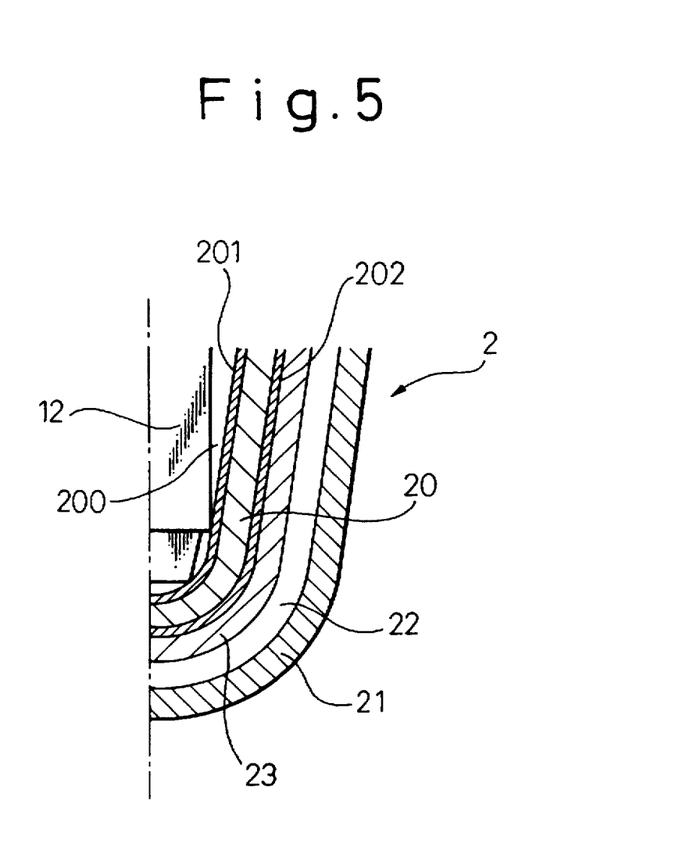
FIG. 5 is a schematical cross-sectional illustration of the detecting element of Example 1.

As shown in FIG. 5, the detecting element 2 has a surface layer 21 on the outside with a contact angle larger than the contact angle of the solid electrolyte 20. Also, the surface layer 21 is composed of BN particles, and has a thickness of 60 µm and a porosity of 50%.

The detecting element 2 has a cup-shaped $ZrO_1$ solid electrolyte 20 provided with an outer electrode 202 made of a platinum film of the outside and an inner electrode 201 on the inside which faces an air chamber 200. On the surface of the outer electrode 202 there are provided, for protection of the outer electrode 202, a protective coating layer 23 made of spinel and a trap layer 22 made of alumina on the surface of the coating layer 23.

Also, the above-mentioned surface layer 21 is provided on the surface of the trap layer 22. The contact angle of the trap layer 22 is smaller than the contact angle of the surface layer 21.

A method of forming the surface layer 21 will now be explained.

First, an inorganic binder containing an alumina sol and a dispersing agent containing aluminum nitrate is mixed with BN particles with an average grain size of 8 µm, to form a slurry.

The slurry is adheared onto the trap layer 22 of the detecting element 2 by dipping to a thickness of 60 µm, and then dried. It is then fired at a temperature of 500° C. for one hour.

This produces a detecting element 2 with the above-mentioned surface layer 21.

Furthermore, as shown in FIG. 4, the detecting element 2 of the oxygen concentration detector 1 according to this embodiment has an enlarged section 29 on the side thereof, and is supported in the housing 10 by the enlarged section 29. At the upper end of the enlarged section 29, a powdered sealant 101 is pressure packed by a pad 102 and insulator 103.

A measuring gas chamber 169 is constructed at the lower end of the housing 10, and double protective covers 161, 162 are provided to protect the lower end of the detection element 2.

The upper end of the housing 10 has three covers covering the top of the detecting element 2, the covers are provided with air inlets for introducing air into the air chamber 200 of the detecting element 2, and on oil-repellent filter 11 is provided at the air inlets.

The three covers consist of a protective cover 13 which is caulked to the top end of the housing 10 via a ring 104, a dust cover 14 formed over the protective cover 13, and a filter cover 15 situated outside the dust cover 14 via the oil-repellent filter 11.

Air inlets 140, 150 are also formed in the dust cover 14 and the filter cover 15, and the oil-repellent filter 11 is imposed between them opposite the air inlets 140, 150.

Figure 6:
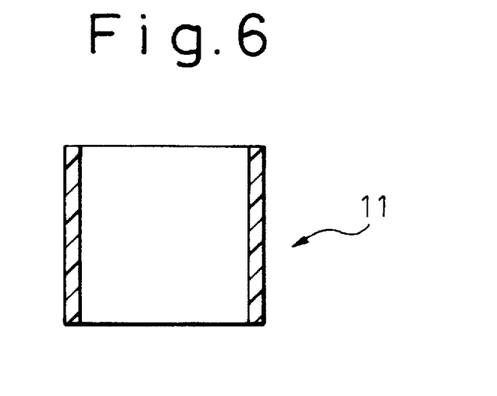
FIG. 6 is a cross-sectional view of the oil-repellent filter of Example 1.
Figure 7:
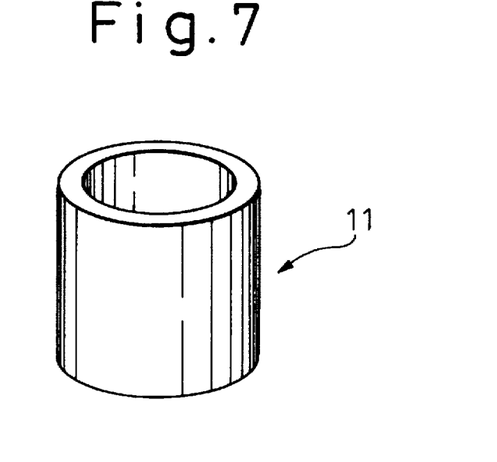
FIG. 7 is a perspective view of the oil-repellent filter of Example 1.

As shown in FIGS. 6 and 7, the oil-repellent filter 11 consists of a porous PTFE resin molded into a pipe shape. Since this oil-repellent filter 11 is caulked between the dust cover 14 and filter cover 15, it is slightly deformed as shown in FIG. 4.

The effect of this embodiment will now be explained.

The oxygen concentration detector 1 according to this embodiment has a surface layer 21 with a large contact angle on the outside of the detecting element 2.

As a result, even when the detecting element 2 contacts with water droplets penetrating into the measuring gas chamber 169, the above-mentioned surface layer 21 repels the water droplets, thus alleviating the thermal shock on the solid electrolyte 20 by the water droplets, and preventing water-induced cracking of the detecting element 2.

Consequently, according to this embodiment there is provided an oxygen concentration detector wherein water-induced cracking does not occur in the detecting element.

The oxygen concentration detector according to this embodiment is provided with a oil-repellent filter 11 opposite the air inlets 140, 150 in the dust cover 14 and filter cover 15, which admits air but has the property of repelling low-surface-tension liquids including, of course, water. This prevents reduction in the oxygen concentration detectability which occurs due to lack of oxygen in the air chamber 200 (oxygen deficiency phenomenon) when oil, detergents, corrosion inhibitors, etc. penetrate through the air inlets 140, 150, causing consumption of oxygen by combustion inside the oxygen concentration detector 1.

EXAMPLE 2

Figure 8:
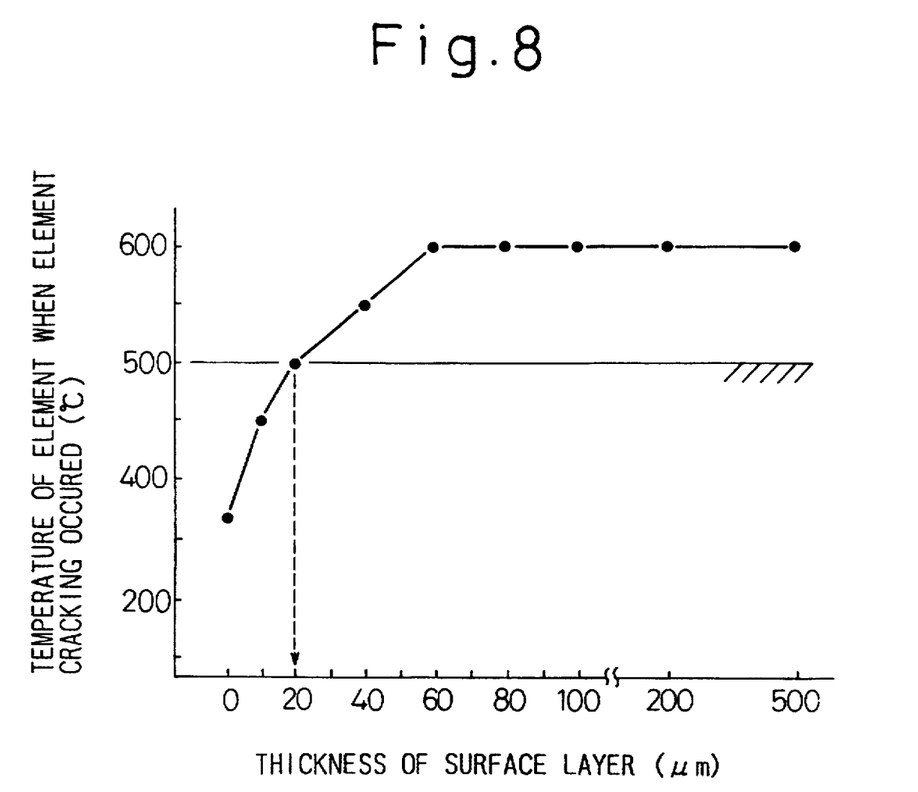
FIG. 8 is a graph showing the relationship between thickness of the surface layer of the detecting element and the temperature at which water-induced cracking occurs, according to Example 2.

This embodiment will be explained with reference to FIG. 8 and Tables 1 to 4, using comparison samples to describe the performance of the detecting element of the present invention, i.e. the relationship between the surface layer thickness, porosity, temperature at which water-induced cracking of the components, etc. occurs, surface layer adhesion strength, etc.

First, the relationship between the thickness of the surface layer and the temperature at which water-induced cracking occurs will be explained with reference to FIG. 8, using sample 4 (though with different surface layer thicknesses) listed in Table 1 below. The horizontal axis of FIG. 8 is surface layer thickness, and the vertical axis is the temperature at which water-induced cracking occurred upon dropping 0.001 cc of water onto the heated detecting element.

As this graph demonstrates, when the surface layer thickness is less than 20 μm, water-induced cracking occurs at a detecting element temperature of less than 500° C.

This shows that the surface layer thickness must be at least 20 μm, and preferably at least 60 μm.

Tables 1 to 4 give the evaluation results for samples 1–4 according to the invention and comparison samples C1–C5, of detecting elements having surface layers with different materials, thicknesses and porosity.

Samples 1–14 and comparison samples C1–C5 all have the different surface layer materials (wt %), porosity (%) and thicknesses (μm) listed in Tables 1 and 2. The surface layers of samples 1–12 and C1–C4 are constructed of simple particles of BN, etc. The surface layers of samples 13 and 14 and comparison sample C-5 are constructed of materials containing alumina as a binder in addition to BN. All of the above-mentioned surface layers were formed by dipping in slurry composed of the respective materials and organic binders, followed by drying and sintering (500° C./h).

As shown in Tables 3 and 4, the evaluation of the performance of the samples 1–14 and comparison samples C1–C5 included examination of the water-induced cracking, and of adhesion strength of the surface layer on the detecting element, initial response to oxygen detection, and contamination resistance.

The occurrence of water-induced cracking was examined upon preheating the detecting element to 500° C. the dropping 0.001 cc of water thereon. In Tables 3 and 4, samples in which no water-induced cracking occurred are indicated with "o", and those in which it occurred are indicated with "x".

The adhesion strength and contamination resistance tests are conducted by first mounting oxygen concentration detectors incorporating the above-mentioned samples and comparison samples in the exhaust system of a 2000 cc in-line 6-cylinder engine. The engine is alternately driven for 30 minutes at rotational speeds of 4000 rpm and 2500 rpm. The element temperature is maintained between 500° C. and 750° C. during this time. The fuel used for the driving is 0.5 wt % engine oil and unleaded gasoline containing a purifying agent.

The adhesion strengths listed in Tables 3 and 4 were measured by the taping method, evaluating as "o" those samples with 20% or less peeled area and as "x" those with over 20%.

The contamination resistance was measured with an engine rotational speed of 1100 rpm and a detecting element temperature kept at 400° C., evaluating as "o" those samples with a frequency change rate of less than 10% and as "x" those with a change rate of greater than 10%.

The initial response was measured with an engine rotational speed of 1100 rpm and a detecting element temperature kept at 400° C. ±10° C., measuring the response time, i.e. The time required for the output to change from 0.6 V to 0.3 V when switching between λ=0.9 and λ=1.1 (λ being the excess air ratio). In Tables 3 and 4, the evaluated response times are indicated with "O" for samples of 150 ms or less, with "Δ" for those of greater than 150 ms to 200 ms and with "x" for those of greater than 200 ms.

The results of the measurements in Tables 3 and 4 are all "O" for samples 1–14 according to the invention.

In contrast, C1 which had a surface layer porosity of less than 20% was inferior from the standpoint of initial response and contamination resistance, and C4 which had a porosity of greater than 90% had inferior adhesion strength. Also, C2 which had a thin surface layer exhibited water-induced cracking, and C3 which had a thick surface layer exhibited low adhesion strength and an inferior initial response.

Furthermore, C5 which had a high alumina content exhibited water-induced cracking.

Thus, it is clear from this embodiment that samples 1–14 were excellent detecting elements with no water-induced cracking.

TABLE 1

| Sample No. Example | Material | Porosity (%) | Thickness (μm) |
| --- | --- | --- | --- |
| 1 | BN 100% | 20 | 60 |
| 2 | BN 100% | 30 | 60 |
| 3 | BN 100% | 50 | 20 |
| 4 | BN 100% | 50 | 60 |
| 5 | BN 100% | 50 | 200 |
| 6 | BN 100% | 50 | 500 |
| 7 | BN 100% | 70 | 200 |
| 8 | BN 100% | 80 | 200 |
| 9 | BN 100% | 90 | 200 |
| 10 | $CaF_2$ 100% | 50 | 60 |
| 11 | $TiB_2$ 100% | 50 | 60 |
| 12 | $ZrB_2$ 100% | 50 | 60 |
| 13 | BN 90% + $Al_2O_3$ 10% | 50 | 60 |
| 14 | BN 80% + $Al_2O_3$ 20% | 50 | 60 |

TABLE 2

| Sample No. Comparative Example | Material | Porosity (%) | Thickness (μm) |
| --- | --- | --- | --- |
| C1 | BN 100% | 10 | 60 |
| C2 | BN 100% | 50 | 10 |
| C3 | BN 100% | 50 | 700 |
| C4 | BN 100% | 95 | 200 |
| C5 | BN 70% + $Al_2O_3$ 30% | 50 | 60 |

TABLE 3

| Sample No. Example | Water induced cracking | Adhesion strength | Initial response | Contamination resistance |
| --- | --- | --- | --- | --- |
| 1 | O | O | O | O |
| 2 | O | O | O | O |
| 3 | O | O | O | O |
| 4 | O | O | O | O |
| 5 | O | O | O | O |
| 6 | O | O | O | O |
| 7 | O | O | O | O |
| 8 | O | O | O | O |
| 9 | O | O | O | O |
| 10 | O | O | O | O |
| 11 | O | O | O | O |
| 12 | O | O | O | O |
| 13 | O | O | O | O |
| 14 | O | O | O | O |

TABLE 4

| Sample No. Comparative Example | Water-induced cracking | Adhesion strength | Initial response | Contamination resistance |
| --- | --- | --- | --- | --- |
| C1 | O | O | Δ | × |
| C2 | ×O | O | O | |
| C3 | O | × | Δ | O |
| C4 | O | × | O | O |
| C5 | × | O | O | O |

EXAMPLE 3

Figure 9:
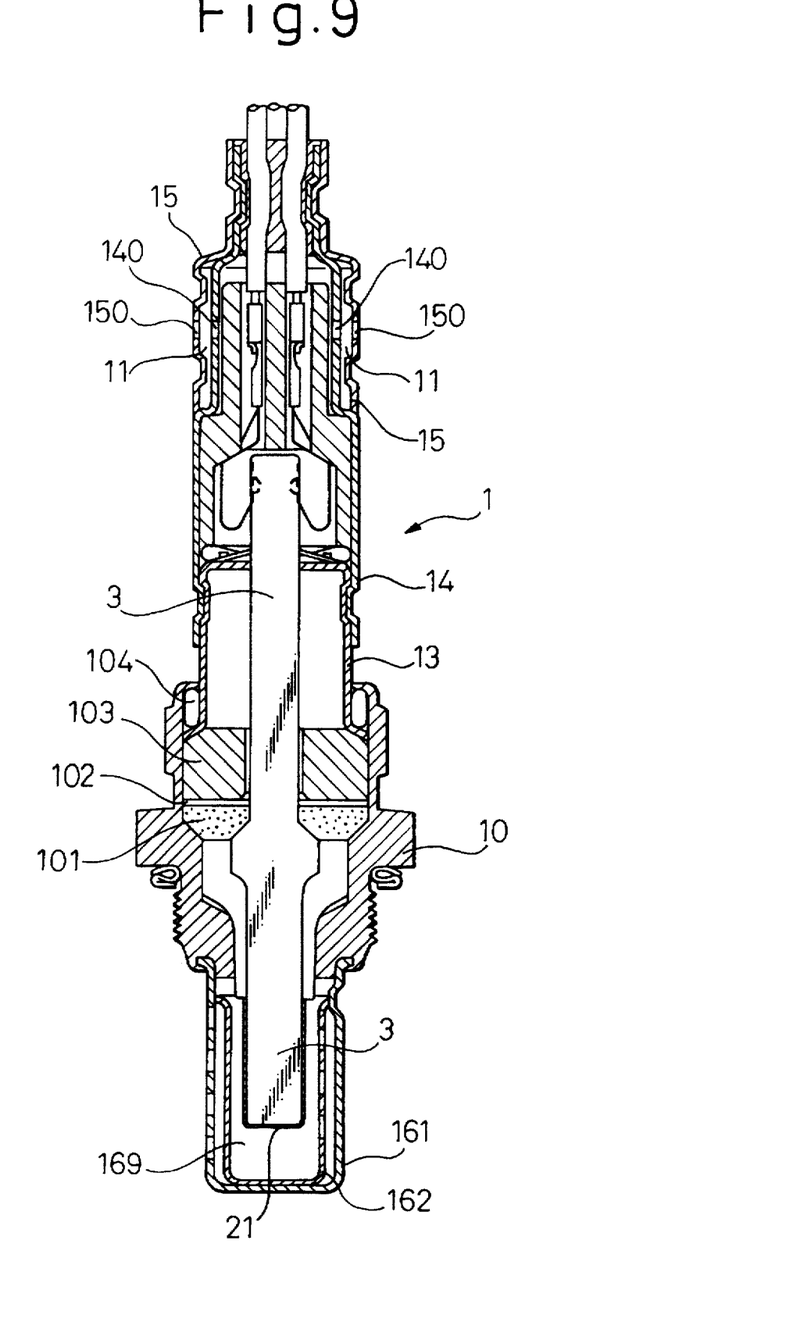
FIG. 9 is a cross-sectional illustration of an oxygen concentration detector with a layered detecting element, according to Example 3.
Figure 10:
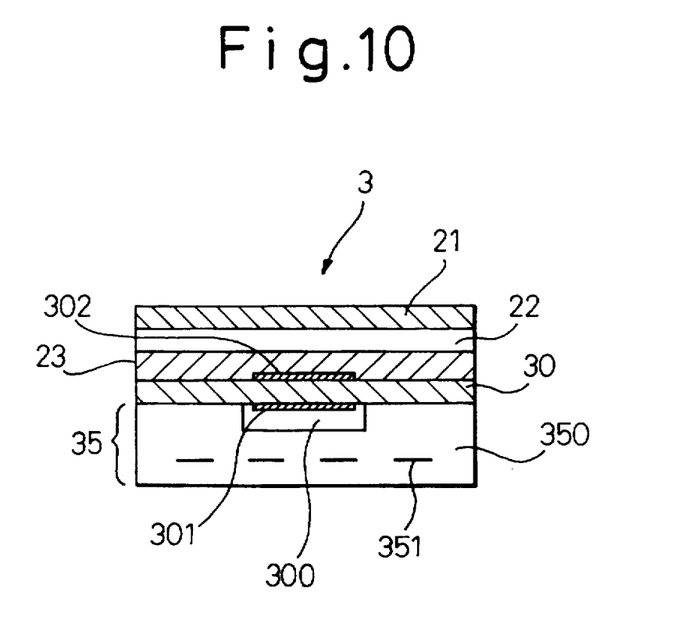
FIG. 10 is a cross-sectional view of the layered detecting element of Example 3.

This embodiment, shown in FIGS. 9 and 10, is an oxygen concentration detector 1 with a laminar detecting element 3.

The oxygen concentration detector 1 according to this embodiment comprises a laminar detecting element 3 inserted in a housing 10 and a heater 35 as heating means provided integrally with the detecting element 3.

The heater 35 is made of a ceramic body 350 in which are embedded heating elements 351.

The heater 35 is laminated with a sheet-like solid electrolyte 30 and the solid electrolyte 30 and the heater 35 form an air chamber 300. An inner electrode 301 is provided on the solid electrolyte 30 facing the air chamber 300.

Meanwhile, an outer electrode 302 is provided on the outside of the solid electrolyte 30. Over the surface of the outer electrode 302 there are formed a coating layer 23 and a trap layer 22 for protection. On the surface of the trap layer 22 there is provided a surface layer 21 which has a contact angle larger than the contact angle of the trap layer.

The rest of the detector is as described in Example 1.

The oxygen concentration detector 1 according to this embodiment also has the same effects as Example 1.

The detector element 3 of this embodiment was provided with a surface layer 21 covering the surface of the trap layer 22 of the detecting element 3, but the surface layer 21 may be provided over the entire detecting element 3 so as to also cover the ceramic body 350 composing the heater 35.

Such a construction makes it possible to prevent water-induced cracking of the ceramic body 350.

EXAMPLE 4

Figure 11:
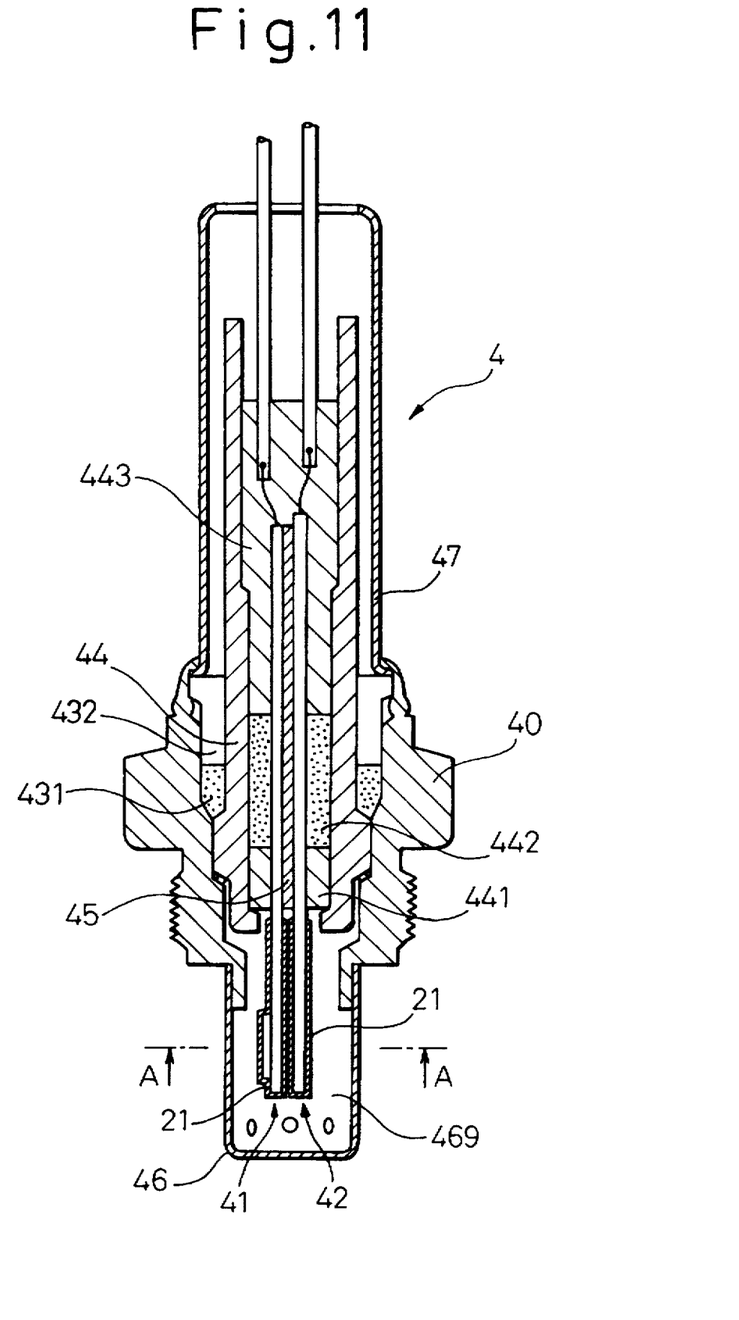
FIG. 11 is a cross-sectional illustration of the oxygen concentration detector of Example 4 wherein the detecting element and the heater are separate.
Figure 12:
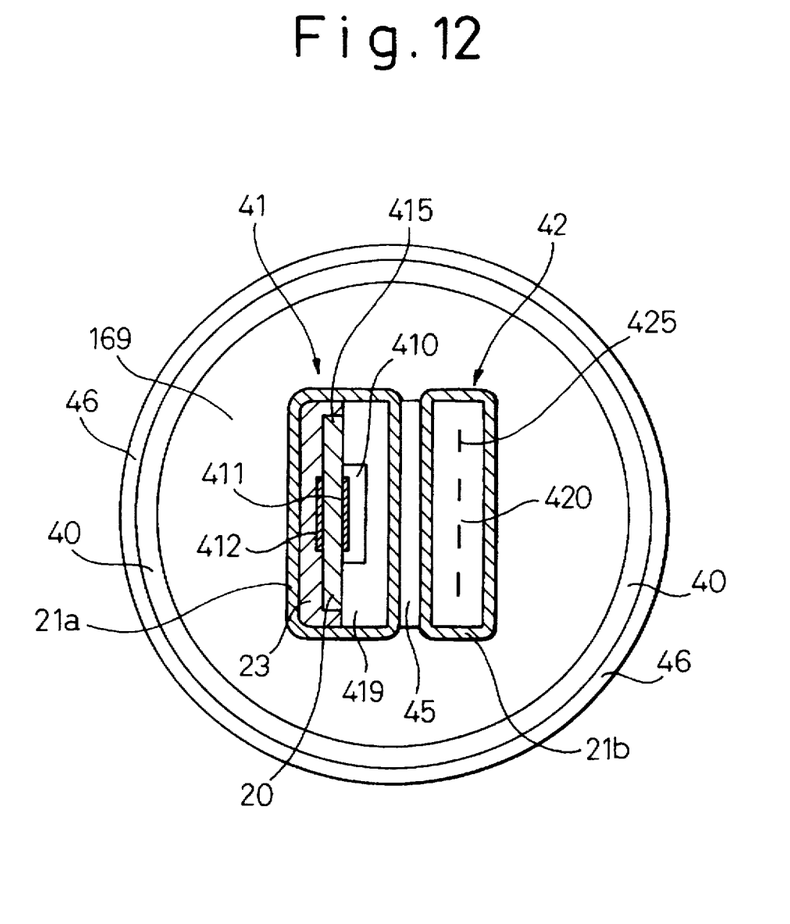
FIG. 12 is a cross-sectional view of FIG. 11 taken along line A—A.

This embodiment, shown in FIGS. 11 and 12, is an oxygen concentration detector 4 with a heater 42 outside the detecting element 41.

The oxygen concentration detector 4 comprises a detecting element 41 made of a solid electrolyte 415, which is inserted in a housing 40 via an inner cover 44, and a heater 42 to heat the detecting element 41.

The heater 42 is adjacently situated outside the detecting element 41, and it has a first surface layer 21a on the surface of the detecting element 41 with a larger contact angle than the contact angle of the coating layer 23 and a second surface layer 21b on the outside of the heater 42 with a larger contact angle than the contact angle of the heater surface.

The oxygen concentration detector 4 is provided with a measuring gas side cover 46 at the lower end of the housing 40 which forms a measuring gas chamber 469, and a protective cover 47 at the upper end.

A supporter 441, powdered sealant 442 and insulator 443 are successively laminated between the inner walls of the detecting element 41 and heater 42 and the inner cover 44, while a powdered sealant 431 is pressure packed by a spacer 432 between the inner cover 44 and the housing 40.

The detecting element 41 and the heater 42 are anchored to each other with ceramic cement 45.

As shown in FIG. 12, the detecting element 41 has a sheet-like solid electrolyte 415 situated against a ceramic substrate 419, and the solid electrolyte 415 and ceramic substrate 419 form an air chamber 410.

An inner electrode 411 is provided on the solid electrolyte 415 facing the air chamber 410. An outer electrode 412 is also provided outside the solid electrolyte 415. The surface of the outer electrode 412 is provided with a coating layer 23 to protect it.

The heater 42 is constructed with heating elements 425 and a ceramic body 420 covering them.

The entire surface of the detecting element 41 and heater 42 which is not protected by the inner cover 44, i.e. the entire section thereof which is exposed in the measuring gas chamber 469, is provided with a first surface layer 21a and a second surface layer 21b having a large contact angle.

The rest of the detector is as described in Example 1.

In the oxygen concentration detector according to this embodiment, the first and second surface layers 21a, 21b having large contact angles are formed on both the detecting element 41 and heater 42. It is thus possible to prevent water-induced cracking in both parts due to contact with water. The other effects are the same as in Example 1.

EXAMPLE 5

Figure 13:
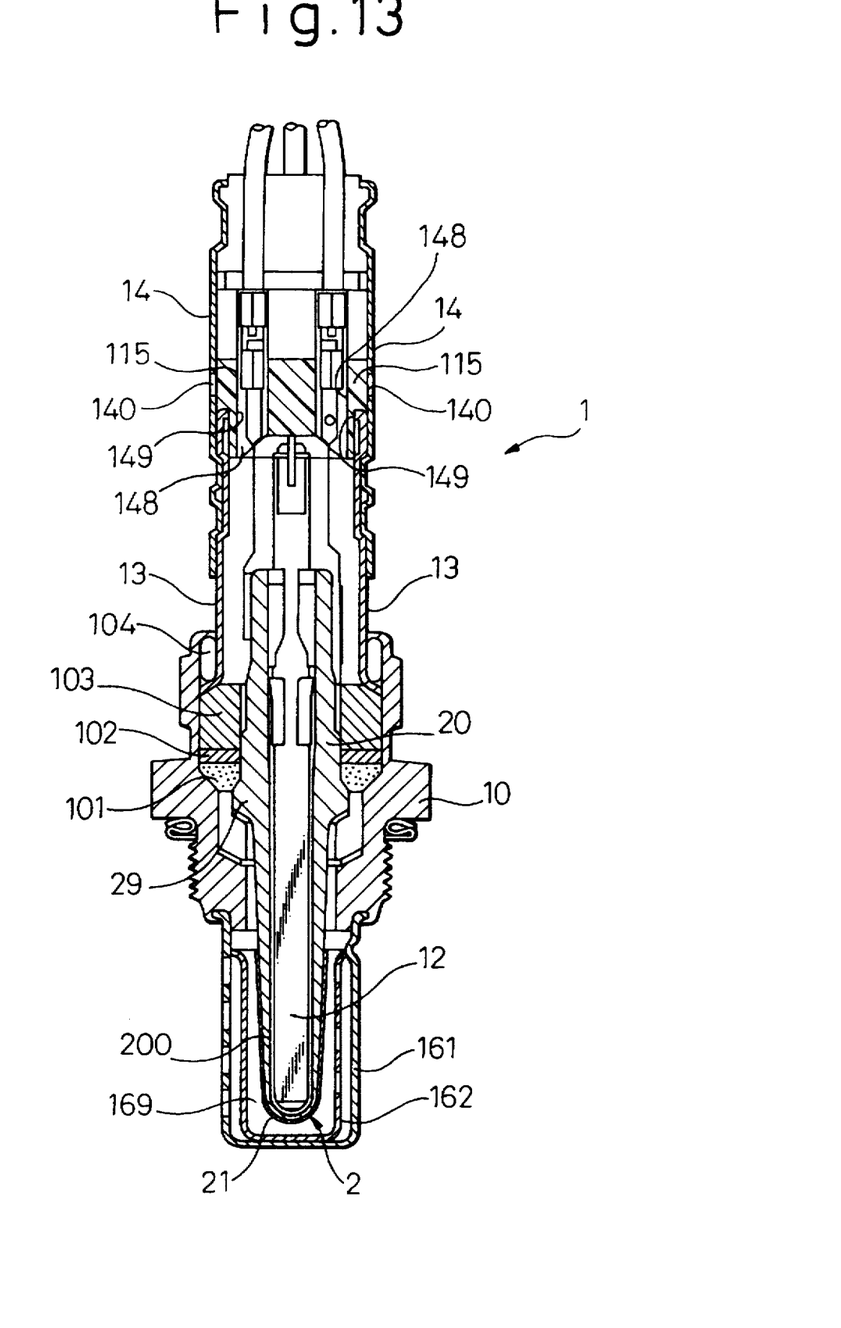
FIG. 13 is a cross-sectional illustration of an oxygen concentration detector of Example 5 which has a block-shaped oil-repellent filter.

This embodiment, shown in FIG. 13, is an oxygen concentration detector 1 which employs a block-shaped oil-repellent filter 115.

The oxygen concentration detector 1 according to this embodiment is constructed with a detecting element 2 inserted in a housing 10, a protective cover 13 which is caulked to the top end of the housing 10, and a dust cover 14 covering the top of the protective cover 13.

A roughly cylindrically-shaped oil-repellent filter 115 is situated in a fitting section 149 provided at the upper end of the dust cover 14, facing the air inlets 140 formed in the dust cover 14. The oil-repellent filter 115 is provided with through-holes 148 to allow placement of output terminals for the detecting element 2.

The rest of the detector is as described in Example 1.

According to this embodiment, the oxygen concentration detector 1 which comprises a detecting element 2 made of a solid electrolyte 20 which is inserted in the housing 10 and a heating element 12 for heating the detecting element 2, is characterized by having a cover 14 which covers the top of the detecting element 2 at the top of the housing 10, and by being provided with air inlets 140 in the cover 14 which admit air into the air chamber 200 of the detecting element 2 and an oil-repellent filter 115 at the air inlets 140.

Furthermore, this oxygen concentration detector exhibits the effect of preventing reduction in the efficiency of oxygen concentration detection which occurs due to a lack of oxygen in the air chamber 200 (oxygen deficiency) when oil, detergents (during car washing), corrosion inhibitors, etc. penetrate through the air inlets 140, causing consumption of oxygen by combustion inside the oxygen concentration detector 1.

We claim:

1. An oxygen concentration detector which comprises
   a housing,
   a detecting element comprising a solid electrolyte inserted in said housing, and
   heating means for heating said detecting element,
   wherein the outer surface of said detecting element is provided with a surface layer comprising particles of one or more materials selected from the group consisting of BN, $CaF_2$, NbC, $ZrB_2$, $TiB_2$ and talc, and the contact angle of the outer surface of said surface layer is larger than the contact angle of the outer surface of said detecting element with which said surface layer directly contacts, said contact angles being measured using a 5 μl water droplet.

2. The oxygen concentration detector of claim 1, wherein a protective layer is provided between said detecting element and said surface layer, which protects an electrode provided on the surface of said detecting element and has a smaller contact angle than the contact angle of said surface layer.

3. The oxygen concentration detector of claim 2, wherein a trap layer is provided between said protective layer and said surface layer, which has a larger porosity than the porosity of said protective layer and has a smaller contact angle than the contact angle of said surface layer.

4. The oxygen concentration detector of claim 1, wherein the thickness of said surface layer is between 20 and 500 μm.

5. The oxygen concentration detector of claim 1, wherein the porosity of said surface layer is between 20 and 90%.

6. The oxygen concentration detector of claim 1, wherein said surface layer contains alumina.

7. An oxygen concentration detector which comprises
   a housing,
   a detecting element comprising a solid electrolyte inserted in said housing, and
   heating means for heating said detecting element,
   wherein said heating means is situated on the outside of the detecting element, and the outer surface of said heating means and detecting element has a surface layer whose contact angle is larger than that of said solid electrolyte, said contact angles being measured using a 5 μl water droplet, said surface layer comprising particles of one or more materials selected from the group consisting of BN, $CaF_2$, NbC, ZrB, $TiB_2$ and talc.

8. An oxygen concentration detector which comprises
   a detecting element comprising a solid electrolyte in the form of a cylinder which is open at one end and closed at the other,
   a measuring electrode provided on the surface of said detecting element, and
   a protecting layer provided on said measuring electrode,
   wherein a surface layer is provided which covers said protecting layer and has a contact angle larger than the contact angle of said protecting layer, said contact angles being measuring using a 5 μl water droplet, said surface layer comprising particles of one or more materials selected from the group consisting of BN, $CaF_2$, NbC, $ZrB_2$, $TiB_2$ and talc.

9. The oxygen concentration detector of claim 8, wherein a trap layer is formed between said protective layer and said surface layer which has a larger porosity than the porosity of said protective layer and has a smaller contact angle than the contact angle of said surface layer.

10. The oxygen concentration detector according to claim 8, wherein said surface layer further comprises alumina particles.

11. An oxygen concentration detector according to claim 8, wherein the detection element includes a heating element.

12. An oxygen concentration detector which comprises
    a detecting element comprising a solid electrolyte in the form of a sheet, an electrode formed on the surface of said detecting element, a protective layer formed on said electrode, a heating element layered on said detecting element to heat said detecting element, and a surface layer which is provided on the outer surface of said heating element and has a larger contact angle than the contact angle of the surface of said heating element, said contact angles being measured using a 5 µl water droplet, said surface layer comprising particles of one or more materials selected from the group consisting of BN, $CaF_2$, NbC, $ZrB_2$, $TiB_2$ and talc.

13. The oxygen concentration detector according to claim 12, further comprising another surface layer which is provided so as to cover said protective layer and has a larger contact angle than the contact angle of said protective layer, said contact angles being measured using a 5 µl water droplet.

14. The oxygen concentration detector according to claim 13, wherein a trap layer is formed between said protective layer and said another surface layer, said trap layer having a larger porosity than the porosity of said protective layer and a smaller contact angle than the contact angle of said another surface layer.

15. The oxygen concentration detector according to claim 13, wherein said another surface layer comprises particles of one or more materials selected from the group consisting of BN, $CaF_2$, NbC, $ZrB_2$, $TiB_2$ and talc.

16. The oxygen concentration detector according to claim 13, wherein said another surface layer further contains alumina particles.

* * * * *